(12) United States Patent
Feller

(10) Patent No.: US 8,042,994 B1
(45) Date of Patent: Oct. 25, 2011

(54) SPECIFIC HEAT METER WITH IMPROVED ACCURACY

(76) Inventor: Murray F Feller, Micanopy, FL (US)

( * ) Notice: Subject to any disclaimer, the term of this patent is extended or adjusted under 35 U.S.C. 154(b) by 0 days.

(21) Appl. No.: 12/941,099

(22) Filed: Nov. 8, 2010

(51) Int. Cl.
*G01N 25/20* (2006.01)
*G01N 17/00* (2006.01)

(52) U.S. Cl. .......................................... 374/43; 374/31
(58) Field of Classification Search .................. 374/43, 374/31
See application file for complete search history.

(56) References Cited

U.S. PATENT DOCUMENTS

| | | | |
|---|---|---|---|
| 3,317,822 A * | 5/1967 | Watson | 324/457 |
| 3,412,359 A * | 11/1968 | Schwyn et al. | 338/30 |
| 3,986,385 A * | 10/1976 | Johnston et al. | 374/23 |
| 4,686,857 A * | 8/1987 | Kato | 73/304 R |
| 4,813,270 A | 3/1989 | Baillie | |
| 4,944,035 A * | 7/1990 | Aagardl et al. | 702/136 |
| 5,031,444 A * | 7/1991 | Doutre et al. | 73/19.07 |
| 5,606,864 A * | 3/1997 | Jones | 62/139 |
| 6,023,969 A | 2/2000 | Feller | |
| 6,241,383 B1 | 6/2001 | Feller | |
| 6,257,004 B1 * | 7/2001 | Gendron et al. | 62/129 |
| 7,775,706 B1 | 8/2010 | Feller | |

* cited by examiner

*Primary Examiner* — Lisa Caputo
*Assistant Examiner* — Mirellys Jagan
(74) *Attorney, Agent, or Firm* — David Kiewit

(57) ABSTRACT

The accuracy of instruments used to measure the specific heat of heat transfer fluids is limited by the accumulation of bubbles, debris or loose surface films on an active measurement surface. Accumulated bubbles, debris or loose film may be reduced or eliminated by using an agitator to cause relative motion between a working fluid and an active surface of a specific heat sensor. The accumulation of bubbles, debris or loose film may also be reduced or eliminated by electrolytically cleaning an electrically conductive heat transfer surface.

7 Claims, 3 Drawing Sheets

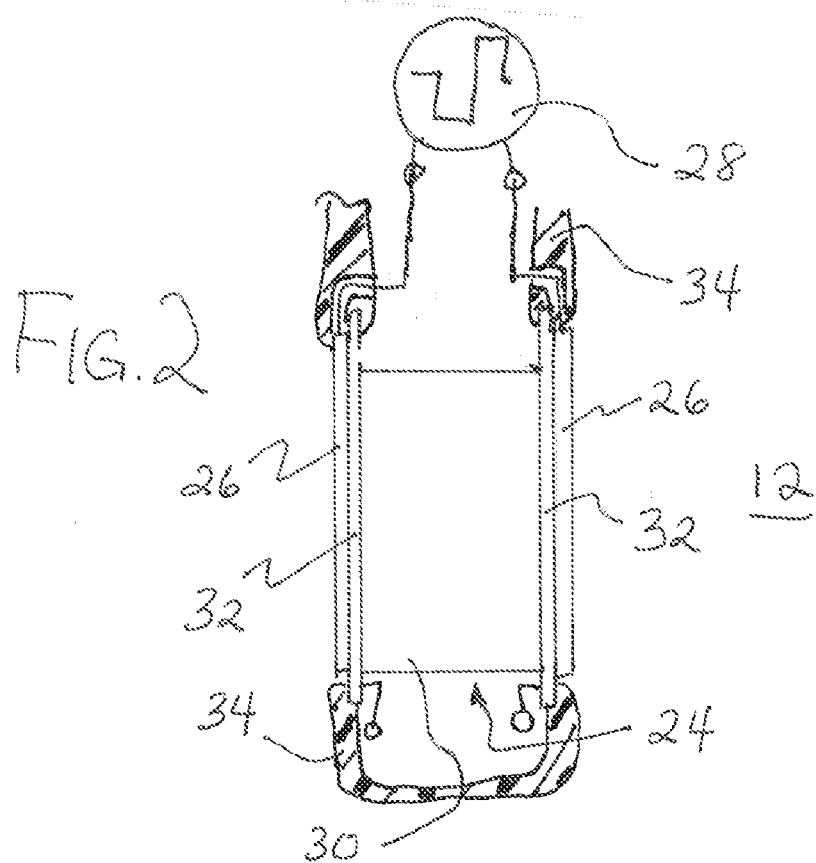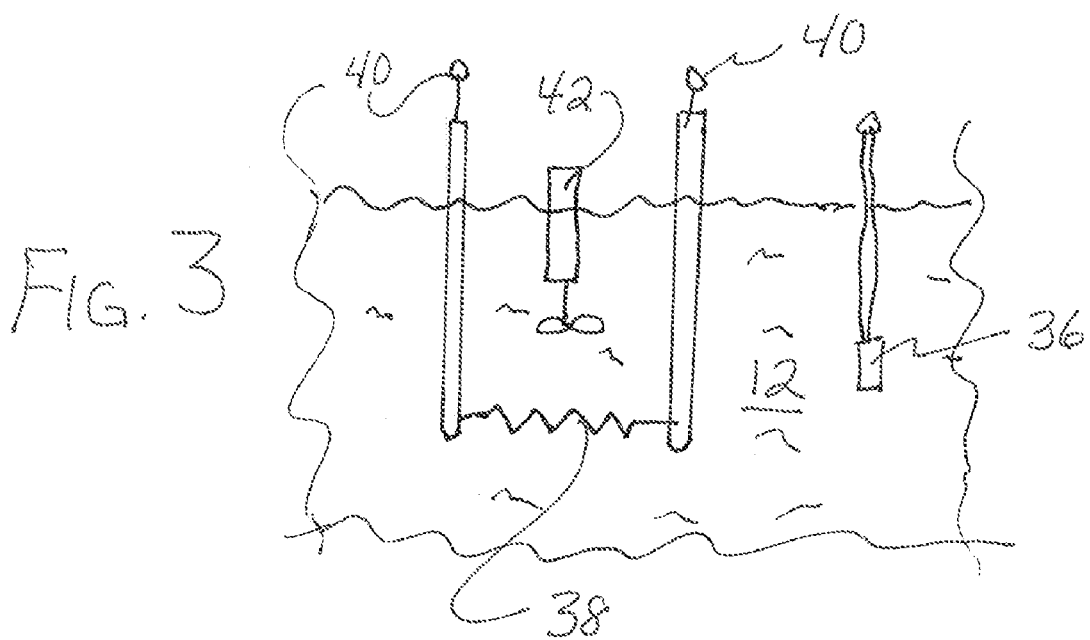

SPECIFIC HEAT METER WITH IMPROVED ACCURACY

BACKGROUND OF THE INVENTION

The present invention deals generally with calorimetry and more specifically with apparatus and method for improving calorimetric measurements by defining and controlling the sensing area across which a heat flux occurs. The subject matter of the present invention relates to that of the inventor's U.S. patent application Ser. No. 12/941,101, entitled "Asymmetric Specific Heat Meter".

BACKGROUND INFORMATION

The accuracy of instruments used to measure the specific heat of heat transfer fluids is limited by the accumulation of bubbles, debris or loose surface films on an active measurement surface. All of these contaminants reduce the effective area contacting the fluid and thereby reduce the amount of heat transferred to the fluid. Thus, these contaminants lead to the measured specific heat of the fluid being less than the true value.

In some known measurement methods chemicals are added to a sample of the working fluid to reduce the formation or attachment of bubbles. This approach is undesirable because the specific heat of the sample may be changed from that of the working fluid.

The heat transfer surfaces may also be manually wiped clean and/or abraded prior to each measurement. Variations in the results of manual cleaning also lead to uncertainty in the reliability of the subsequent specific heat measurement. Moreover, manual approaches are not applicable if specific heat is to be monitored automatically over an extended time interval.

BRIEF SUMMARY OF THE INVENTION

The accumulation of bubbles, debris or loose film may be reduced or eliminated by using an agitator to cause relative motion between a working fluid and an active surface of a specific heat sensor. The accumulations are essentially washed off by mechanical action.

In some embodiments of the invention the agitator acts on the sensor. In other embodiments of the invention the agitator acts directly on the fluid.

Agitators that act directly on a sensor include, but are not limited to: piezoelectric actuators, electromechanical buzzers, solenoids, voice coils and electric motors. Agitators that act directly on the fluid include, but are not limited to various motor-driven impellers and pumps as well as piezoelectric insonifiers.

An actuator may be operated periodically, for example at the beginning of a measurement cycle and periodically thereafter, or continuously in a precision manner to provide the equivalent of a regulated fluid flow past the active surfaces.

The accumulation of bubbles, debris or loose film may also be reduced or eliminated by using electrolytic cleaning of an electrically conductive heat transfer surface. The electrolytic cleaning may be provided by applying either a DC or an AC voltage to a heat transfer surface. In some embodiments, the voltage is applied between one or more heat transfer surfaces and a separate cleaning electrode immersed in the working fluid being measured. In other embodiments the voltage is applied between multiple heat transfer surfaces.

One aspect of the invention is that it improves a specific heat measurement instrument having at least one electrically conductive heat transfer surface wetted by a fluid when the instrument is in use. This improvement comprises providing both an electric power supply and an agitator. The electric power supply is operable to selectively supply a voltage to each conductive heat transfer surface. The agitator is operable to cause relative motion between the heat transfer surface (or surfaces) and the fluid.

Another aspect of the invention is that it provides apparatus for measuring the specific heat of a fluid. This apparatus comprises a thermoelectric device and an electric power supply. The thermoelectric device has first and second ends in respective thermal contact, at respective electrically conductive surfaces, with a fluid when the apparatus is in use. The electric power supply is operable to selectively supply respective voltages to the two electrically conducting surfaces.

Yet another aspect of the invention is that it provides apparatus for measuring the specific heat of a fluid, where the apparatus comprises both a thermoelectric element and an agitator. The thermoelectric element has two ends, each of which is in respective thermal contact with the fluid when the apparatus is in use. The agitator is operable to move the thermoelectric element relative to the fluid.

Still a further aspect of the invention is that it provides an improved specific heat measurement instrument. This instrument has at least one electrically conductive heat transfer surface wetted by a fluid when the instrument is in use. The instrument is operable to determine the specific heat of the fluid by measuring a thermal response to a known energy input. The instrument also comprises an electric power supply operable to selectively supply a respective voltage to each at least one conductive wettable surface.

Those skilled in the art will recognize that the foregoing broad summary description is not intended to list all of the features and advantages of the invention. Both the underlying ideas and the specific embodiments disclosed in the following Detailed Description may serve as a basis for alternate arrangements for carrying out the purposes of the present invention and such equivalent constructions are within the spirit and scope of the invention in its broadest form. Moreover, different embodiments of the invention may provide various combinations of the recited features and advantages of the invention, and that less than all of the recited features and advantages may be provided by some embodiments.

BRIEF DESCRIPTION OF THE SEVERAL VIEWS OF THE DRAWING

FIG. 2 is a partly schematic detail view of a portion of an embodiment of the invention using a thermoelectric module (TEM) as a sensing element.

FIG. 3 is a schematic view of a portion of an embodiment of the invention using a metallic sensing element.

DETAILED DESCRIPTION OF A PREFERRED EMBODIMENT

Figure 1:
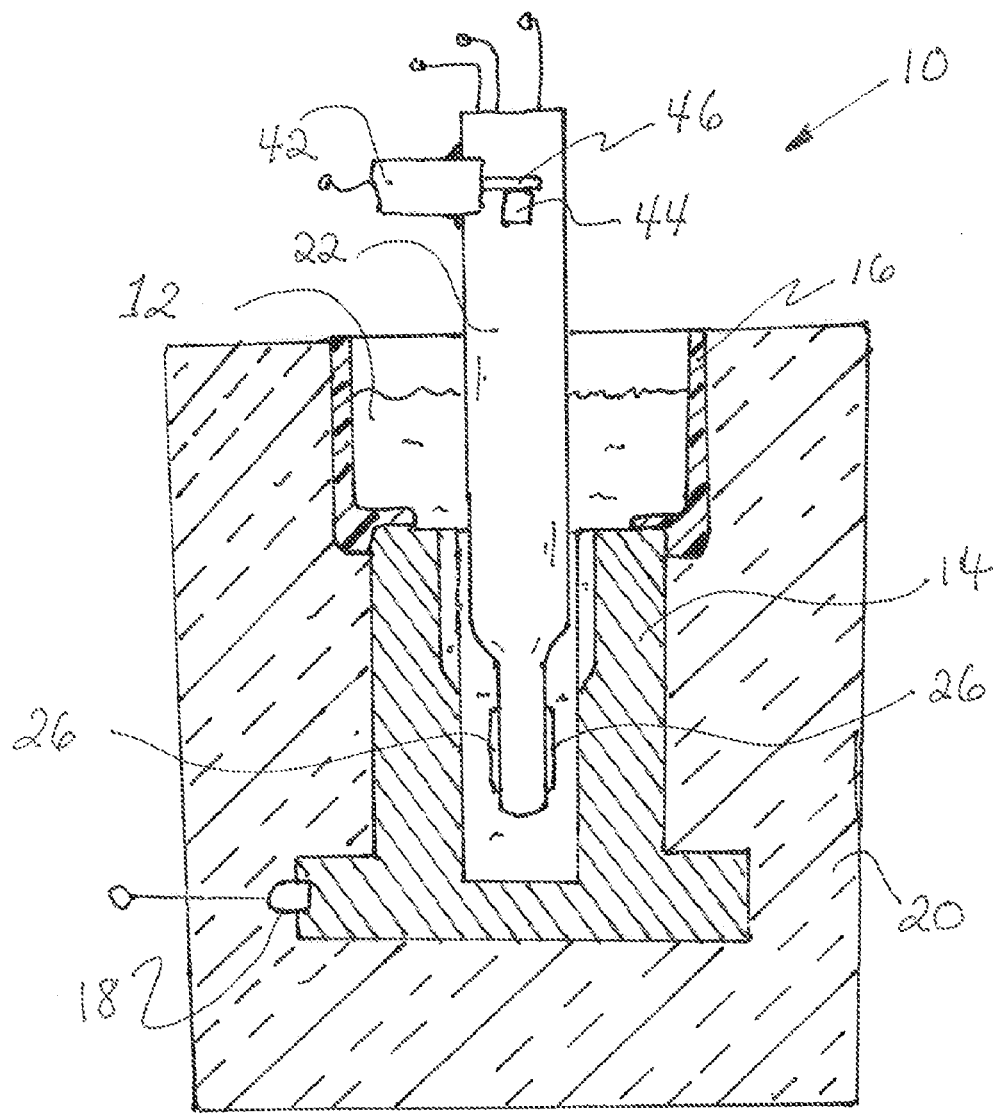
FIG. 1 is a partly schematic composite view of a static sampling embodiment of the invention, the view showing, in elevation, a specific heat sensing probe disposed in a sample vessel, shown in cross section.

The specific heat of a working fluid may be determined in a static measurement by withdrawing a sample of the fluid from a heat exchange system and placing it in a sample chamber 10 of the sort generally depicted in FIG. 1. Alternately, the specific heat may be determined from sensors immersed in a flowing fluid 12 as taught by the inventor in his U.S. Pat. No. 7,775,706, the disclosure of which is incorporated herein by reference.

In a static specific heat measurement the sample chamber 10 may comprise a cup 14 that is preferably made of a material, such as aluminum, that has a high thermal conductivity. The cup may have a reservoir 16 extending above it. A temperature sensor 18 may be embedded in the cup and used to determine the temperature at which the specific heat measurement is being made. The cup and reservoir assembly may be embedded in a thermally insulating jacket 20 that may be made of a foamed plastic. Alternately one may choose to insulate only the sides of the cup 14 and thermally couple the bottom of the cup to a thermoelectric heat pump (not shown) that can be used to control the temperature of the fluid being measured.

In these static embodiments a heat flow sensing probe 22 is inserted into the sample of working fluid 12 to make the specific heat measurement. In the preferred embodiment depicted in FIG. 1, and in selected detail in FIG. 2, the probe comprises a thermoelectric module (TEM) 24 in contact with two electrically conducting surfaces 26 arranged to contact the fluid and to define the active area for heat flow. In this preferred embodiment the conducting surfaces are connected to an electric power supply 28 operable to selectively apply a voltage between them so as to cause electrolysis in the working fluid. Electrical connection to the liquid is of course, not applicable when the liquid is an electrical insulator.

A preferred heat sensing element is depicted schematically in FIG. 2. It comprises a TEM 24 of a known sort having a plurality of thermocouples 30 arrayed between two alumina end plates 32. Metallization patterns (not shown) on the facing sides of the end plates 32 provide electrical connections to the thermocouples 30, which are electrically connected in series and physically arrayed parallel to each other so that when a voltage is applied to the TEM 24 all of the hotter sides of the thermocouples abut one of the plates and all of the colder sides abut the other. In addition to the conventional metallization, the preferred TEM has respective metal films or foils 26 on each of the outer surfaces of its end plates. When the TEM is fitted or potted into a probe housing 34 the exposed metal surfaces define the heat transfer areas.

In a preferred approach, after a probe is inserted into the cup of working fluid, the plates 26 thermally coupled to the TEM 24 are energized electrolytically for a short period, typically one to three minutes, to improve their wetting action before the heat transfer measurement is made. In a particular preferred method of operation, a 1 Hz square wave of 20 volt peak-to-peak amplitude is effective in providing the desired wetting action in good quality water. In this case small bubbles can be observed attached to and rising from the plates. The signal frequency and/or magnitude of the power supply output can both be adjusted for similar results with other liquids.

Although the preferred operating mode calls for sequentially applying positive and negative polarities to each active surface, this is not required. Suitable electrolytic action can be achieved by a variety of bipolar and unipolar arrangements.

Although the preferred arrangement calls for conduction through the working fluid 12 between two active surfaces, electrolytic cleaning can also be provided in an arrangement using a separate electrode 36. This allows for use of a probe having a single active surface area. A probe comprising a metal resistor of known surface area 38 exposed to the working fluid 12, is schematically depicted in FIG. 3. An additional external electrode 36 is provided. In operation, the two probe electrodes 40 are electrically connected together and the electrolytic voltage is applied between the probe electrodes 40 and the external one 36.

Agitation is also effective at cleaning an active surface of a specific heat probe. In the preferred embodiment depicted in FIG. 1, an electromechanical agitator 42 is mechanically coupled to a portion of a specific heat probe and used in conjunction with electrolytic cleaning.

A preferred electromechanical agitator 42 is a motor having an axially asymmetric weight 44 on its output shaft 46. Devices of this sort are commonly used in cellular telephones to provide a noise-free 'vibrate' alerting signal. Although a vibrating motor is preferred, one may use many sorts of electromechanical agitators mechanically coupled to the probe including, but not limited to piezoelectric elements, voice coils, electromechanical buzzers, and solenoids. Moreover, the electromechanical agitator 42 may be coupled to the fluid, rather than to the probe and may be an impeller, pump, insonifier, etc. as schematically depicted in FIG. 3. That is, the essential requirement of the agitator is that it can produce relative motion between the fluid 12 and the active probe surface(s) 26. Whether this is done by acting directly on the probe or on the fluid is inconsequential.

Although electrolytic cleaning and agitation can be used separately, a preferred approach is to use both mechanisms. In a specific case, the two plates of a TEM sensor 24 were connected to a 1 Hz supply at 20 V peak-to-peak for one to three minutes while operating a preferred agitation motor connected to the probe. The specific heat measurement was then made as quickly as possible before bubbles could reform. In this preferred operation the motor is operated until after the TEM has stabilized, as indicated by repeated operations and/or operational intervals producing no change in the specific heat measurement. By contrast, as long as the probe surface remains wet with the liquid being tested, the electrolytic wetting operation typically needs be performed only once, before the first measurement in a series of measurements.

Figure 4:
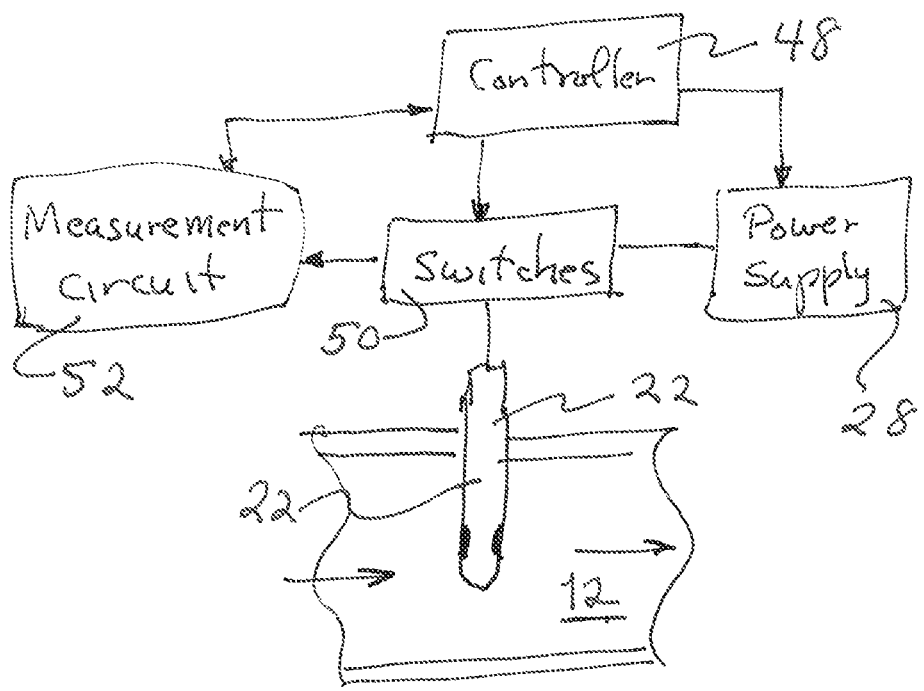
FIG. 4 of the invention is a schematic block diagram of an automated embodiment of the invention.

The method and apparatus of the invention are not restricted to use with a static measure on a working fluid sample removed from a heat transfer system. Agitation and electrolytic cleaning can be applied, separately or together, to a specific heat sensor immersed in a flowing working fluid 12. In the depiction of FIG. 4 a controller 48 can used to operate a switch array 50 so that during a pre-measurement interval an electrolysis power supply 28 can be connected to the active area(s) of a probe while the measurement circuitry 52 is disconnected. Subsequently, the measurement circuit 52 is connected to the probe 22 while the power supply 28 is disconnected. Thus, the active surface(s) can be cleaned immediately prior to each specific heat measurement.

Although the present invention has been described with respect to several preferred embodiments, many modifications and alterations can be made without departing from the invention. Accordingly, it is intended that all such modifications and alterations be considered as being within the spirit and scope of the invention as defined in the attached claims.

The invention claimed is:

1. Apparatus for measuring the specific heat of a fluid, the apparatus comprising:
   a thermoelectric module comprising a plurality of thermocouples arrayed between two electrically insulating end plates, the thermocouples electrically connected in series and physically arrayed parallel to each other so that when a selected DC current is passed through the thermoelectric module all hotter sides of the thermocouples abut one of the plates and all colder sides abut the other, the two insulating end plates in respective thermal contact, at respective electrically conductive surfaces electrically insulated from the thermocouples, with a fluid when the apparatus is in use;

an electric power supply operable to selectively supply respective voltages to the two electrically conducting surfaces; and an electromechanical agitator operable to move the thermoelectric module relative to the fluid when the fluid is present.

2. The apparatus of claim 1 wherein the power supply is connected between the two electrically conducting surfaces so as to supply distinct respective voltages thereto.

3. The apparatus of claim 1 wherein the power supply is connected so as to supply a common voltage to the two electrically conducting surfaces and a distinct voltage to a separate electrode.

4. The apparatus of claim 1 wherein the electro-mechanical agitator comprises an electric motor having an axially asymmetric weight on an output shaft thereof.

5. Apparatus for measuring the specific heat of a fluid, the apparatus comprising: a thermoelectric module comprising a plurality of thermocouples arrayed between two end plates, the thermocouples electrically connected in series and physically arrayed parallel to each other so that when a selected DC current is passed through the thermoelectric module all hotter sides of the thermocouples abut one of the plates and all colder sides abut the other, each of the two end plates in respective thermal contact with the fluid when the apparatus is in use; and an electromechanical agitator operable to move the thermoelectric module relative to the fluid, the agitator comprising an electric motor having an axially asymmetric weight on an output shaft thereof.

6. The apparatus of claim 5 wherein each end of the thermoelectric module is in contact with the fluid, when the fluid is present, at a respective electrically conducting surface, the apparatus further comprising an electric power supply connected to the electrically conducting surfaces so as to supply distinct respective voltages thereto.

7. The apparatus of claim 5 wherein each end of the thermoelectric module is in contact with the fluid, when the fluid is present, at a respective electrically conducting surface, the apparatus further comprising an electric power supply connected to the electrically conducting surfaces so as to supply a common voltage to the two electrically conducting surfaces and a distinct voltage to a separate electrode.

* * * * *